United States Patent
Ray, II et al.

(10) Patent No.: US 9,468,599 B2
(45) Date of Patent: *Oct. 18, 2016

(54) COMPOSITION AND METHOD FOR COMPOUNDED THERAPY

(75) Inventors: Jay Richard Ray, II, Conroe, TX (US); Charles D. Hodge, Conroe, TX (US)

(73) Assignee: CMPD LICENSING, LLC, Conroe, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/448,088

(22) Filed: Apr. 16, 2012

(65) Prior Publication Data

US 2013/0165429 A1    Jun. 27, 2013

Related U.S. Application Data

(63) Continuation of application No. 13/409,738, filed on Mar. 1, 2012, now abandoned, which is a continuation-in-part of application No. 13/337,598, filed on Dec. 27, 2011, now abandoned.

(51) Int. Cl.
| | |
|---|---|
| A61K 31/54 | (2006.01) |
| A61K 31/495 | (2006.01) |
| A61K 31/50 | (2006.01) |
| A61K 31/135 | (2006.01) |
| A61K 9/00 | (2006.01) |
| A61K 31/5415 | (2006.01) |
| A61K 31/167 | (2006.01) |
| A61K 31/53 | (2006.01) |
| A61K 31/7048 | (2006.01) |
| A61K 9/06 | (2006.01) |

(52) U.S. Cl.
CPC .............. *A61K 9/0014* (2013.01); *A61K 9/06* (2013.01); *A61K 31/167* (2013.01); *A61K 31/53* (2013.01); *A61K 31/5415* (2013.01); *A61K 31/7048* (2013.01)

(58) Field of Classification Search
USPC ...................... 514/183, 226.5, 248
See application file for complete search history.

(56) References Cited

U.S. PATENT DOCUMENTS

| | | | |
|---|---|---|---|
| 4,562,060 A | 12/1985 | Broberg et al. | |
| 4,937,078 A | 6/1990 | Mezei et al. | |
| 5,993,836 A | 11/1999 | Castillo | |
| 6,248,789 B1 | 6/2001 | Weg | |
| 6,290,986 B1 * | 9/2001 | Murdock et al. | 424/449 |
| 6,299,902 B1 * | 10/2001 | Jun | A61K 9/0014 424/443 |
| 6,410,062 B1 | 6/2002 | Callaghan et al. | |
| 7,166,641 B2 | 1/2007 | Lee et al. | |
| 8,535,738 B2 | 9/2013 | Collins et al. | |
| 2001/0029257 A1 * | 10/2001 | Murdock | A61K 9/0014 514/220 |
| 2003/0124176 A1 | 7/2003 | Hsu et al. | |
| 2004/0265364 A1 * | 12/2004 | Ozturk | A61K 31/195 424/449 |
| 2005/0038062 A1 | 2/2005 | Burns et al. | |
| 2005/0187212 A1 * | 8/2005 | Ohki | A61K 9/7053 514/226.5 |
| 2006/0140986 A1 | 6/2006 | Fita | |
| 2006/0223788 A1 | 10/2006 | Cathcart | |
| 2007/0065463 A1 | 3/2007 | Aung-Din | |
| 2007/0093420 A1 | 4/2007 | Yeomans et al. | |
| 2007/0116730 A1 | 5/2007 | Simmons et al. | |
| 2007/0269393 A1 | 11/2007 | Wepfer | |
| 2007/0269465 A9 | 11/2007 | Fita | |
| 2008/0233183 A1 | 9/2008 | McCook et al. | |
| 2009/0162421 A1 | 6/2009 | Geisslinger et al. | |
| 2010/0016436 A1 | 1/2010 | Staniforth et al. | |
| 2010/0080797 A1 | 4/2010 | Yeomans et al. | |
| 2010/0160299 A1 | 6/2010 | Baker, Jr. et al. | |
| 2010/0184817 A1 | 7/2010 | Wolicki | |
| 2010/0221309 A1 | 9/2010 | Myers et al. | |
| 2010/0226972 A1 * | 9/2010 | Lutz | 424/450 |
| 2010/0286205 A1 | 11/2010 | McCarron et al. | |

(Continued)

FOREIGN PATENT DOCUMENTS

| | | |
|---|---|---|
| EP | 0964552 | 8/2009 |
| IN | 2005/MU00373 | * 2/2007 |

(Continued)

OTHER PUBLICATIONS

Remington: The Science and Practice of Pharmacy 21st Edition, Published 2005. pp. 745-746, 759-760, 768-770 and 871-876.*

(Continued)

*Primary Examiner* — Wu-Cheng Winston Shen
*Assistant Examiner* — George W Kosturko
(74) *Attorney, Agent, or Firm* — Akerman LLP

(57) ABSTRACT

The present embodiments relate to topically delivered compounded medications. A transdermal cream may provide the effective topical administration of multiple medications simultaneously; may include low concentrations of local anesthetics, a NSAID, an anticonvulsant, and/or other active ingredients; and may include lidocaine, prilocaine, meloxicam, and lamotrigine and/or topiramate. Alternatively, the transdermal cream may include a lidocaine/prilocaine base cream to which is added a fine powder of one or more ground up medications to form a compounded medication. The compounded medication in powder form may be generated from grinding up tablets of NSAIDs, anticonvulsants, nerve depressants, antidepressants, muscle relaxants, NMDA receptor antagonists, opiate or opioid agonists, and/or other agents. The compounded medication in powder form may include meloxicam, lamotrigine, topiramate, other active ingredients, and DMSO or Sterile Water for Irrigation. In another aspect, the present embodiments relate to methods of compounding medications and transdermal creams or gels.

5 Claims, 2 Drawing Sheets

(56) References Cited

U.S. PATENT DOCUMENTS

| | | | |
|---|---|---|---|
| 2010/0287884 | A1 | 11/2010 | Seshadri et al. |
| 2011/0015229 | A1 | 1/2011 | Zhang et al. |
| 2011/0028460 | A1 | 2/2011 | Kisak et al. |
| 2011/0033545 | A1 | 2/2011 | Wang |
| 2011/0250212 | A1 | 10/2011 | Yeomans et al. |
| 2011/0257257 | A1 | 10/2011 | Shapira et al. |
| 2013/0085171 | A1 | 4/2013 | Ray |
| 2013/0165430 | A1 | 6/2013 | Ray et al. |
| 2015/0148305 | A1 | 5/2015 | Ray et al. |
| 2015/0359740 | A1 | 12/2015 | Ray |
| 2015/0359767 | A1 | 12/2015 | Ray |
| 2015/0359768 | A1 | 12/2015 | Ray |

FOREIGN PATENT DOCUMENTS

| | | | |
|---|---|---|---|
| IN | 373/MUM/2005 | * | 3/2007 |
| IN | 2005MU00373 | * | 3/2007 |
| JP | 7309749 | | 11/1995 |
| WO | WO 2004/110423 | | 12/2004 |
| WO | WO 2013/048453 | | 4/2013 |
| WO | WO 2013/101949 | | 7/2013 |

OTHER PUBLICATIONS

Lehmann, H. A., et al. Meloxicam: A Toxicology Review. Inflammopharmacology. vol. 4, pp. 105-123. Published 1996.*
Remington: The Science and Art of Pharmacy 21st Edition. Published 2005. pp. 745-746, 759-760, 768-770 and 871-876.*
Erickson, M.A., et al. Pharmacy Times. Published onlined Jan. 2005.*
Richie, G.E., et al. Water for Pharmaceutical Purposes. USPC Official. Published Feb. 11, 2008.*
Renno, S.I. et al., Journal of Clinical Oncology ASCO Annual Meeting Proceedings vol. 24 No. 18S. Published 2006.*
Renno et al (J. Clin. Oncology, ASCO Annual Meeting Abstract 2006 vol. 24 No. 18S.*
Nahata et al., (Am. J. Health Syst. Pharm. vol. 56, pp. 240-242, published 1999).*
Baclofen Suspension (Sick Kids Pharmacy, published Apr. 2007).*
Renno et al (J. Clin. Oncology, ASCO Annual Meeting Abstract 2006 vol. 24 No. 18S).*
Erickson et al., (Pharmacy Times, published online Jan. 1, 2005).*
Sick Kids Pharmacy (published Apr. 2007).*
Nahata et al., (Am. J. Health Syst. Pharm. vol. 56, pp. 240-242, published 1999, abstract provided).*
Gennaro, A.R., et al., Remington: Practice of the Science and Pharmacy 19th Edition. pp. 1516-1517. Published 1995.*
Richie et al., (USP Water for Pharmaceutical Purposes, published Feb. 11, 2008).*
Patent Cooperation Treaty, "International Search Report and Written Opinion" U.S. International Searching Authority, by Officer Young, Lee W., in PCT Application No. PCT/US2012/071846, Document of 19 pages, dated Mar. 5, 2013.
PCCA, T3 Sodium Dilution (1:1000), Fall 2011 Issue, Sep. 1, 2011, PCCA Webpage, http://ww.rxinsider.com/20waystarticles/pcca_article.pdf].
Abstract Only: Merskey H., Pharmacological approaches other than opioids in chronic non-cancer pain management, Acta Anaethesiol Scand, Jan. 1997, 41 (1 Pt 2), 187-190.
Abstract Only: Dissanayake et al., Spermine modulation of specific [3H]-gabapentin binding to the detergent-solubilized porcine cerebral cortex alpha 2 delta calcium channel subunit, Br J Pharmacol, Mar. 1997, 120(5), 833-840.
Abstract Only: Boardman et al., Topical gabapentin in the treatment of localized and generalized vulvodynia, Sep. 2008, 112(3): 579-585.
Prommer, Eric F, Topical analgesic combinations for bortezomib neuropathy, Journal of Pain and Symptom Management, Mar. 2009, 37(3), pp. e3-e5.
Abstract Only: Guindon et al., Recent advances in the pharmacological management of pain, Drugs, 2007, 67(15), 2121-2133.
Alsarra, Ibrahim A., Evaluation of proniosomes as an alternative strategy to optimize piroxicam transdermal delivery, Journal of Microencapsulation, 2008, 1-7, iFirst.
Penzes et al., Topical absorption of piroxicam from organogels—in vitro and in vivo correlations, International Journal of Phamieceutics, 2005, 298, 47-54.
Abstract Only: Park et al., Transdermal delivery of piroxicam using microemulsions, Arch Pharm Res., Feb. 2005, 28 (2), 243-248.
Abstract Only: Hong et al., Suprascapular nerve block or a piroxicam patch for shoulder tip pain after day case laparoscopic surgery, Eur J Anaesthesiol, Mar. 2003, 20(3), 234-238.
Doliwa et al., Transdermal Iontophoresis and skin retention of piroxicam from gels containing piroxicam: hydroxypropyl-beta-cyclodextrin complexes, Drug Development and Industrial Pharmacy, 2001, 27(8), 751-758, Marcel Dekker, Inc.
Abstract Only: Cordero et al., In vitro based index of topical anti-inflammatory activity to compare a series of NSAIDs, Eur J Pharm Biopharm, Mar. 2001, 51(2), 132-142.
Abstract Only: Ritchie LD, A clinical evaluation of flurbiprofen LAT and piroxicam gel: a multicentre study in general practice, Clin Rheumatol, May 1996, 15(3), 243-247.
Abstract Only: Marks et al., Plasma and cutaneous drug levels after topical application of piroxicam gel: a study in healthy volunteers, 1994, 7(6), 340-344.
Abstract Only: Russell Al., Piroxicam 0.5% topical gel compared to placebo in the treatment of acute soft tissue injuries: a double-blind study comparing efficacy and safety, Clin Invest Med, Feb. 1991, 14(1), 35-43.
Abstract Only: Akinturk et al., Effect of piroxicam gel for pain control and inflammation in Nd:YAG 1064-nm laser hair removal, J Eur Acad Dermatol Veneraol, Mar. 2007, 21(3), 380-383.
Abstract Only: Attia et al., Transbuccal permeation, anti-inflammatory activity and clinical efficacy of piroxicam formulated in different gels, Int J Pharm, May 19, 2004, 276(1-2), 11-28.
Abstract Only: Dutta et al., Piroxicam gel, compared to EMLA cream is associated with less pain after venous cannulation in volunteers, Can J Anaesth, Oct. 2003, 50(8), 775-778.
Abstract Only: Ambade KW, Formulation and evaluation of flurbiprofen microemulsion, Curr Drug Deliv., Jan. 2008, 5 (1), 32-41.
Bhaskar et al., Lipid nanoparticles for transdermal delivery of flurbiprofen: formulation, in vitro, ex vivo and in vivo studies, Lipids in Health and Disease, Feb. 26, 2009, 8(6), 1476-1511.
Abstract Only: Pelfini et al., Flurbiprofen in gel: study of acceptability, tolerability and evaluation of its allergenic potential, G Ital Dermatol Venereol, Sep. 1989, 124(9), XLIII-XLVI.
Abstract Only: Suresh et al., Intracrevicular application of 0.3% Flurbiprofen gel and 0.3% Triclosan gel as anti-inflammatory inflammatory agent. A comparative clinical study, Indian J Dent Res., Apr.-Jun. 2001, 12(2), 105-112.
Abstract Only: El Gendy et al., In vitro release studies of flurbiprofen from different topical formulations, Drug Dev Ind Pharm, Aug. 2002, 28(7), 823-31.
Esparza et al., Topical ketoprofen TDS patch versus diclofenac gel: efficacy and tolerability in benign sport related soft-tissue injuries, Br J Sports Med, 2007, 41, 134-139.
Abstract Only: Mazia Res B., Topical ketoprofen patch, Drugs R D, 2005, 6(6), 337-344.
Abstract Only: Audeval-Gerard et al., Pharmacokinetics of ketoprofen in rabbit after a single topical application, Eur J Drug Metab Pharmacokinet, Jul.-Dec. 2000, 25(3-4), 227-230.
Abstract Only: Moretti et al. In vitro release and antiinflammatory activity of topical formulations of ketoprofen, Boll Chim Farm, Mar.-Apr. 2000, 139(2), 67-72.
Abstract Only: Airaksinen et al., Ketoprofen 2.5% gel versus placebo gel in the treatment of acute soft tissue injuries, Int J Clin Pharmacol Ther Toxicol, Nov. 1993, 31(11) 561-563.
Abstract Only: Baixauli et al., Percutaneous treatment of acute soft tissue lesions with naproxen gel and ketoprofen gel, J Int Med Res, Sep.-Oct. 1990, 18(5), 372-378.

(56) References Cited

OTHER PUBLICATIONS

Abstract Only: Matucci-Cerinic et al., Ketoprofen vs etofenamate in a controlled double-blind study: evidence of topical effectiveness in soft tissue rheumatic pain, Int J Clin Pharmacol Res., 1988, 8(3), 157-160.
Abstract Only: Moghadamnia et al., Evaluation of the effect of locally administered amitriptyline gel as adjunct to local anesthetics in irreversible pulpitis pain, Jan.-Mar. 2009, 20(1), 3-6.
Sandroni et al., Combination gel of 1% amitriptyline and 0.5% ketamine to treat refractory erythromelalgia pain: a new treatment option?, Arch Dermatol, Mar. 2006, 142, 283-286.
Abstract Only: Sawynok et al., Peripheral antinociceptive actions of desipramine and fluoxetine in an inflammatory and neuropathic pain test in the rat, Pain, Aug. 1999, 82(2), 149-158.
Abstract Only: Scott et al., Use of transdermal amitriptyline gel in a patient with chronic pain and depression, Pharmacotherapy, Feb. 1999, 19(2) 236-239.
Abstract Only: Sakai et al., Quantitative and selective evaluation of differential sensory nerve block after transdermal lidocaine, Anesth Anaig., Jan. 2004, 98(1), 248-251.
Abstract Only: Taddio et al., Lidocaine-prilocaine cream versus tetracaine gel for procedural pain in children, Ann Pharmacother, Apr. 2002, 36(4), 687-692.
Abstract Only: Rowbotham et al., Topical lidocaine gel relieves postherpetic neuralgia, Ann Neurol, Feb. 1995, 37 (2), 246-253.
Abstract Only: Shimoda et al., Transdermal application of 10% lidocaine-gel for management of pain associated with herpes zoster, Masui, Aug. 1993, 42(8), 1171-1176.
Abstract Only: Vadivelu et al., Recent advances in postoperative pain management, Yale J Biol Med, Mar. 2010, 83 (1), 11-25.
Okon, Tomasz MD, Ketamine: An introduction for the pain and palliative medicine physician, Pain Physician, May 2007, 10, 493-500.
Abstract Only: Kronenberg RH., Ketamine as an analgesic: parenteral, oral, rectal, subcutaneous, transdermal and intranasal administration, J Pain Palliat Care Pharmacother, 2002, 16(3), 27-35.
Azevedo et al., Transdermal ketamine as an adjuvant for postoperative analgesia after abdominal gynecological surgery using lidocaine epidural blockade, Anesth Analg, 2000, 91, 1479-1482, International Anesthesia Research Society.
Vranken, Jan H., Mechanisms and treatment of neuropathic pain, Central Nervous System Agents in Medicinal Chemistry, 2009, 9, 71-78, Bentham Science Publishers Ltd.
Abstract Only: Canbay et al., Topical ketamine and morphine for post-tonsillectomy pain, Eur J Anaesthesiol, Apr. 2008, 25(4), 287-292.
Lynch et al., Topical amitriptyline and ketamine in neuropathic pain syndromes: An open-label study, The Journal of Pain, Oct. 2005, 6(10), 644-649, The American Pain Society.
Abstract Only: Gammaitoni et al., Topical ketamine gel: possible role in treating neuropathic pain, Pain Med, Mar. 2000, 1(1), 97-100.
Abstract Only: Slatkin et al., Topical ketamine in the treatment of mucositis pain, Pain Med, Sep. 2003, 4(3), 298-303.
Abstract Only: Altman et al., Topical therapy for osteoarthritis: Clinical and pharmacologic perspectives, Postgrad Med, Mar. 2009, 121(2), 139-147.
Roth et al., Efficacy and safety of a topical diclofenac solution in the treatment of primary osteoarthritis of the knee: a randomized, double-blind, vehicle controlled clinical trial, Arch Intern Med, Oct. 11, 2004, 164, 2017-2023, American Medical Association.
Kneer et al., A multiple-dose, open-label, safety, compliance, and usage evaluation study of epicutaneously applied Diractin (ketoprofen in Transfersome) in joint/musculoskeletal pain or soft tissue inflammation, Current Drug Safety2009, 4, 5-10, Bentham Science Publishers, Ltd.
U.S. Appl. No. 61/541,716, filed Sep. 30, 2011, Ray.
U.S. Appl. No. 13/337,598, filed Dec. 27, 2011, Ray et al.
U.S. Appl. No. 13/409,739, filed Mar. 1, 2012, Ray et al.
U.S. Appl. No. 14/996,560, filed Jan. 15, 2016, Ray.
Akarsu S, et al. (2011) Comparison of topical 3% diclofenac sodium gel and 5% imiquimod cream for the treatment of actinic keratoses. Clin Exp.Dermatol. 36(5):479-484.
Akbay BK, et al. (2010). Analgesic efficacy of topical tramadol in the control of postoperative pain in children after tonsillectomy. J Anesth. 24(5):705-708.
Akermark C, et al. (1990) Topical indomethacin in overuse injuries in athletes. A randomized double-blind study comparing Elmetacin with oral indomethacin and placebo. Int J Sports Med. 11(5):393-396.
Alañón F, et al. (2014) Comparison between topical anaesthesia with.cocaine versus lidocaine plus adrenaline for outpatient laser. dacryocystorhinostomy. Arch Soc Esp Oftalmol. 89(2):53-57.
Allegrini A, et al. (2009) Efficacy and safety of piroxicam patch versus piroxicam cream in patients with lumbar osteoarthritis. A randomized, placebo-controlled study. Arzneimittelforschung. 59(8):403-409.
Ambler JJ, et al. (2005) The effect of topical non-steroidal anti-inflammatory cream on the incidence and severity of cutaneous burns following external DC cardioversion. Resuscitation. 65(2):173-178.
Arapoglou V, et al. (2011) Analgesic efficacy of an ibuprofen-releasing foam dressing compared with local best practice for painful exuding wounds. J Wound Care. 20(7):319-320, 322-325.
Arnau B, et al. (2013) Lidocaine-prilocaine (EMLA®) cream as analgesia in hysteroscopy practice: a prospective, randomized, non-blinded, controlled study. Acta Obstet Gynecol Scand. 92(8):978-981.
Assouline M, et al. (1998) A prospective randomized trial of topical soluble 0.1% indomethacin versus 0.1% diclofenac versus placebo for the control of pain following excimer laser photorefractive keratectomy. Ophthalmic Surg Lasers. 29(5):365-374.
Attia MA, et al. (2004) Transbuccal permeation, anti-inflammatory. B&B Compounding Pharmacy. (2010) Pain Management Compounding Available at http://www.bbpharmacy.com/paincompounding.html. (5 pages).
Badalá F, et al. (2004) Effect of topical 0.1% indomethacin solution versus 0.1% fluorometholon acetate on ocular surface and pain control following laser subepithelial keratomileusis (LASEK). Cornea. 23(6):550-553.
Barthel HR, et al. (2009) Randomized controlled trial of diclofenac sodium gel in knee osteoarthritis. Semin Arthritis Rheum. 39(3):203-212.
Barton DL, et al. (2011) A double-blind, placebo-controlled trial of a topical treatment for chemotherapy-induced peripheral neuropathy: NCCTG trial N06CA. Support Care Cancer. 19(6):833-841.
Bernstein JE, et al. (1981) Inhibition of histamine-induced pruritus by topical tricyclic antidepressants. J Am Acad Dermatol. 5(5):582-585.
Bourolias C, et al. (2010) Lidocaine spray vs tetracaine solution for transnasal fiber-optic laryngoscopy. Am J Otolaryngol. 31(2):114-116.
Campbell J, et al. (1994) Evaluation of topical ibuprofen cream in the treatment of acute ankle sprains. J Acid Emerg Med. 11(3):178-182.
Campione E, et al. (2010) Topical treatment of actinic keratoses with piroxicam 1% gel: a preliminary open-label study utilizing a new clinical score. Am J Clin Dermatol. 11(1):45-50.
Christensen TJ, et al. (2013) Lidocaine analgesia for removal of wound vacuum-assisted closure dressings: a randomized double-blinded placebo-controlled trial. J Orthop Trauma. 27(2):107-112.
Cigna E, et al. (2009) Evaluation of polyurethane dressing with ibuprofen in the management of split-thickness skin graft donor sites. In Vivo. 23(6):983-936.
Conaghan PG, et al. (2013) A multicentre, randomized, placebo- and active-controlled trial comparing the efficacy and safety of topical ketoprofen in Transfersome gel (IDEA-033) with ketoprofen-free vehicle (TDT 064) and oral celecoxib for knee pain associated with osteoarthritis. Rheumatology (Oxford). 52(7):1303-1312.

(56) References Cited

OTHER PUBLICATIONS

Coudert AE, et al. (2014) Phase III, randomized, double-blind, placebo-controlled trial of topical 2 % lidocaine for the prevention and treatment of oral mucosal pain in children. Clin Oral Investig. 18(4):1189-1194.
Crowley KL, et al. (1998) Clinical application of ketamine ointment in the treatment of sympathetically maintained pain. Int J Pharm Compd. 2(2):122-127.
Dinsmore WW, et al. (2007) Topical eutectic mixture for premature ejaculation (TEMPE): a novel aerosol-delivery form of lidocaine-prilocaine for treating premature ejaculation. BJU Int. 99(2):369-375.
Dreiser RL, et al. (1994) Flurbiprofen local action transcutaneous (LAT): clinical evaluation in the treatment of acute ankle sprains. Eur J Rheumatol Inflamm. 14(4):9-13.
Dutta A, et al. (2003) Piroxicam gel, compared to EMLA cream is associated with less pain after venous cannulation in volunteers. Can J Anaesth. 50(8):775-778.
Federal Drug Agency. (1996) TOPAMAX—Highlights of Prescribing Information. (27 pages).
Federal Drug Agency. (2010) MOBIC—Highlights of Prescribing Information. (15 pages).
Fibromyalgia General Discussion—"So Many Questionns—Please Read and Advise" (Jan. 15, 2011), available at http://www.fibromyalgia-symptoms.org/forums/fibromyalgia_general_discussion/so_many_questions_please_read_and_advise/.
Fraczek M, et al. (2012) Assessment of the efficacy of topical anesthetics using the tactile spatial resolution method. Acta Dermatovenerol Croat. 20(1):7-13.
Franchi M, et al. (2009) Comparison between lidocaine-prilocaine cream (EMLA) and mepivacaine infiltration for pain relief during perineal repair after childbirth: a randomized trial. Am J Obstet Gynecol. 201(2):186.e1-5.
Franz TJ, et al. (1990) The use of water permeability as a means of validation for skin integrity in in vitro percutaneous-absorption studies. J Invest Dermatol. 94(4):525. (Abstract Only).
Franz TJ, et al. (2008) The cadaver skin absorption mode and the drug development process. Pharmacopeial Forum. 34(5).
Franz TJ, et al. (2009) Use of excised human skin to assess the bioequivalence of topical products. Skin Pharmacol Physiol. 22(5):276-286.
Franz TJ. (1975) Percutaneous absorption on the relevance of in vitro data. J Invest Dermatol. 64(3):190-195.
Funosas ER, et al. (2009) The use of topical subgingival gels of non-steroidal anti-inflammatory drugs (NSAIDs) as an adjunct to non-surgical management of chronic periodontitis. Acta Odontol Latinoam. 22(3):215-219.
Gaviola GC, et al. (2013) A prospective, randomized, double-blind study comparing the efficacy of topical anesthetics in nasal endoscopy. Laryngoscope. 123 (4): 852-858.
Gencer ZK, et al. (2013) Comparison of ropivacaine, bupivacaine, prilocaine, and lidocaine in the management of pain and hemorrhage during nasal pack removal. Am J Rhinol Allergy. 27(5):423-425.
Gerner P, et al. (2003) Topical amitriptyline in healthy volunteers. Reg Anesth Pain Med. 28(4):289-293.
Ginsberg F, et al. (1991) Double-blind, randomized crossover study of the percutaneous efficacy and tolerability of a topical indomethacin spray versus placebo in the treatment of tendinitis. J Int Med Res. 19(2):131-136.
Gupta NK, et al. (2013) Randomized controlled trial of topical EMLA and breastfeeding for reducing pain during wDPT vaccination. Eur J Pediatr. 172(11): 1527-1533.
Gursoy A, et al. (2007) The analgesic efficacy of lidocaine/prilocaine (EMLA) cream during fine-needle aspiration biopsy of thyroid nodules. Clin Endocrinol (Oxf). 66(5):691-694.
Hirsh I, et al. (2007) Tramadol improves patients' tolerance of transrectal ultrasound-guided prostate biopsy. Urology. 69(3):491-494.
Hong JP, et al. (2014) Comparison of analgesic effect of preoperative topical diclofenac and ketorolac on postoperative pain after photorefractive keratectomy. J Cataract Refract Surg. 40(10):1689-1696.
Hopp C, et al. (2012) Clinical efficacy of tetracaine anesthetic paste. Gen Dent. 60(2):e69-73. (Abstract Only).
Hui-Chen F, et al. (2013) The effect of EMLA cream on minimizing pain during venipuncture in premature infants. J Trop Pediatr. 59(1):72-73.
Keppel Hesselink JM, et al. (2013) Treatment of chronic regional pain syndrome type 1 with palmitoylethanolamide and topical ketamine cream: modulation of nonneuronal cells. J Pain Res. 6:239-245.
Kwon YS, et al. (2012) Treatment for postoperative wound pain in gynecologic laparoscopic surgery: topical lidocaine patches. J Laparoendosc Adv Surg Tech A. 22(7):668-673.
Lee HJ, et al. (2013) The effect of buffered lidocaine in local anesthesia: a prospective, randomized, double-blind study. J Hand Surg Am. 38(5):971-975.
Lehman JS, et al. (2008) Effective use of topical amitriptyline hydrochloride 2.5% and ketamine hydrochloride 0.5% for analgesia in refractory proctodynia. J Drugs Dermatol. 7(9):887-889. (Abstract Only).
Liang CL, et al. (2011) Topical anesthetic EMLA for postoperative wound pain in stereotactic gamma knife radiosurgery: a perspective, randomized, placebo-controlled study. Minim Invasive Neurosurg. 54(2):75-78.
Liberty G, et al. (2007) Lidocaine-prilocaine (EMLA) cream as analgesia for hysterosalpingography: a prospective, randomized, controlled, double blinded study. Hum Reprod. 22(5):1335-1339.
Lynch ME, et al. (2003) A pilot study examining topical amitriptyline, ketamine, and a combination of both in the treatment of neuropathic pain. Clin J Pain. 19(5):323-328.
Lynch ME, et al. (2005) Topical 2% amitriptyline and 1% ketamine in neuropathic pain syndromes: a randomized, double-blind, placebo-controlled trial. Anesthesiology. 103(1):140-146.
Machen J, et al. (2002) Efficacy of a proprietary ibuprofen gel in soft tissue injuries: a randomised, double-blind, placebo-controlled study. Int J Clin Pract. 56(2):102-106.
Mansell-Gregory M, et al. (1998) Randomised double blind trial of EMLA for the control of pain related to cryotherapy in the treatment of genital HPV lesions. Sex Transm Infect. 74(4):274-275.
Martens M. (1997) Efficacy and tolerability of a topical NSAID patch (local action transcutaneous flurbiprofen) and oral diclofenac in the treatment of soft-tissue rheumatism. Clin Rheumatol. 16(1):25-31.
Mazières B, et al. (2005) Topical ketoprofen patch (100 mg) for the treatment of ankle sprain: a randomized, double-blind, placebo-controlled study. Am J Sports Med. 33(4):515-523.
Mazières B, et al. (2005) Topical ketoprofen patch in the treatment of tendinitis: a randomized, double blind, placebo controlled study. J Rheumatol. 32(8):1563-1570.
Missotten L, et al. (2001) Topical 0.1% indomethacin solution versus topical 0.1% dexamethasone solution in the prevention of inflammation after cataract surgery. The Study Group. Ophthalmologica. 215(1):43-50.
Moen MD. (2009) Topical diclofenac solution. Drugs. 69(18):2621-2632.
Momo K, et al. (2005) Preparation and clinical application of indomethacin gel for medical treatment of stomatitis. Yakugaku Zasshi. 125(5):433-440.
Nayak R, et al. (2006) Evaluation of three topical anaesthetic agents against pain: a clinical study. Indian J Dent Res. 17(4):155-160.
Oskouee SJ, et al. (2007) Bandage contact lens and topical indomethacin for treating persistent corneal epithelial defects after vitreoretinal surgery. Cornea. 26(10):1178-1181.
Patel RK, et al. (1996) Comparison of ketoprofen, piroxicam, and diclofenac gels in the treatment of acute soft-tissue injury in general practice. General Practice Study Group. Clin Ther. 18(3):497-507.
Peniston JH, et al. (2012) Long-term tolerability of topical diclofenac sodium 1% gel for osteoarthritis in seniors and patients with comorbidities. Clin Intery Aging. 7:517-523.

(56) References Cited

OTHER PUBLICATIONS

Pharmacy OneSource. Simplifi 797—USP Chapter 797 Compliance Management (2 pages), Available at http://www.pharmacyonesource.com/simplifi797/.
Picazo A, et al. (2006) Examination of the interaction between peripheral diclofenac and gabapentin on the 5% formalin test in rats. Life Sci. 79(24):2283-2287.
Poterucha TJ, et al. (2013) Topical amitriptyline combined with ketamine for the treatment of erythromelalgia: a retrospective study of 36 patients at Mayo Clinic. J Drugs Dermatol. 12(3):308-310.
Pöyhiä R, et al. (2006) Topically administered ketamine reduces capsaicin-evoked mechanical hyperalgesia. Clin J Pain. 22(1):32-36.
Predel HG, et al. (2012) Efficacy and safety of diclofenac diethylamine 2.32% gel in acute ankle sprain. Med Sci Sports Exerc. 44(9):1629-1636.
Predel HG, et al. (2013) A randomized, double-blind, placebo-controlled multicentre study to evaluate the efficacy and safety of diclofenac 4% spray gel in the treatment of acute uncomplicated ankle sprain. J Int Med Res. 41(4):1187-1202.
Rahimi M, et al. (2012) Comparison of topical anesthetic cream (EMLA) and diclofenac suppository for pain relief after hemorrhoidectomy: a randomized clinical trial. Surg Today. 42(12):1201-1205.
Rao RD, et al. (2008) Efficacy of lamotrigine in the management of chemotherapy-induced peripheral neuropathy: a phase 3 randomized, double-blind, placebo-controlled trial, N01C3. Cancer. 112(12):2802-2808.
Rashwana S, et al. (2014) Effect of tramadol gargle on postoperative sore throat: A double blinded randomized placebo controlled study. Egyptian J Anaesthesia. 30(3): 235-239.
Rother M, et al. (2013) A randomized, double-blind, phase III trial in moderate osteoarthritis knee pain comparing topical ketoprofen gel with ketoprofen-free gel. J Rheumatol. 40(10):1742-1748.
RovenskýJ, et al. (2001) Treatment of knee osteoarthritis with a topical non-steroidal antiinflammatory drug. Results of a randomized, double-blind, placebo-controlled study on the efficacy and safety of a 5% ibuprofen cream. Drugs Exp Clin Res. 27(5-6):209-221.
Samson D, et al. (2007) Eutectic mixture of local anesthetic (EMLA) decreases pain during humeral block placement in nonsedated patients. Anesth Analg. 105(2):512-515.
Sanabria MR, et al. (2013) Ocular pain after intravitreal injection. Curr Eye Res. 38(2):278-282.
Sanosil. (2010) Sanosil Product Description Sheet. (7 pages).
Segatto MM, et al. (2013) Comparative study of actinic keratosis treatment with 3% diclofenac sodium and 5% 5-fluorouracil. An Bras Dermatol. 88(5):732-738.
Simon LS, et al. (2009) Efficacy and safety of topical diclofenac containing dimethyl sulfoxide (DMSO) compared with those of topical placebo, DMSO vehicle and oral diclofenac for knee osteoarthritis. Pain. 143(3):238-245.
Tekelioglu UY, et al. (2013) Comparison of topical tramadol and ketamine in pain treatment after tonsillectomy. Paediatr Anaesth.
Thaller VT, et al. (2000) The effect of pre-operative topical flurbiprofen or diclofenac on pupil dilatation. Eye (Lond). 14 ( Pt 4):642-645.
Tham EJ, et al. (1994) An assessment of prilocaine as a topical anaesthetic agent for fibreoptic bronchoscopy in comparison with lidocaine. Acta Anaesthesiol Scand. 38(5):442-447.
Tiso RL, et al. (2010) Oral versus topical Ibuprofen for chronic knee pain: a prospective randomized pilot study. Pain Physician. 13(5):457-467.
Titlic M, et al. (2008) Lamotrigine in the treatment of pain syndromes and neuropathic pain. Bratisl Lek Listy. 109(9):421-424. (Abstract Only).
Toker MI, et al. (2006) The effects of topical ketorolac and indomethacin on measles conjunctivitis: randomized controlled trial. Am J Ophthalmol. 141(5):902-905.

TrnayskýK, et al. (2004) Efficacy and safety of 5% ibuprofen cream treatment in knee osteoarthritis. Results of a randomized, double-blind, placebo-controlled study. J Rheumatol. 31(3):565-572.
United States Pharmacopeial Convention. (2013) Official Monograph for Lidocaine and Prilocaine Cream. USP 36: 4115-4117. (3 pages).
United States Pharmacopeial Convention. (2013) Official Monograph for Meloxicam Tablets. USP 36: 4230-4231. (2 pages).
United States Pharmacopeial Convention. (2013) Official Monograph for Topiramate. USP 36: 5431-5434. (4 pages).
Whitefield M, et al. (2002) Comparative efficacy of a proprietary topical ibuprofen gel and oral ibuprofen in acute soft tissue injuries: a randomized, double-blind study. J Clin Pharm Ther. 27(6):409-417.
Wiffen PJ, et al. (2007) Lamotrigine for acute and chronic pain. Cochrane Database Syst Rev. (2):CD006044. (Abstract Only).
Wiffen PJ, et al. (2011) Lamotrigine for acute and chronic pain. Cochrane Database Syst Rev. (2):CD006044. Update in Wiffen PJ, et al. (2013) Lamotrigine for chronic neuropathic pain and fibromyalgia in adults. Cochrane Database Syst Rev. 12:CD006044.
Wiffen PJ, et al. (2013) Topiramate for neuropathic pain and fibromyalgia . In adults. Cochrane Database Syst Rev. 8:CD008314.
Wyllie MG, et al. (2012) The role of local anaesthetics in premature ejaculation. BJU Int. 110(11 Pt C):E943-E948.
Yavas GF, et al. (2007) Preoperative topical indomethacin to prevent pseudophakic cystoid macular edema. J Cataract Refract Surg. 33(5):804-807.
Yeoh, et al. (2012) Pain during venous cannulation: Double-blind, randomized clinical trial of analgesic effect between topical amethocaine and eutectic mixture of local anesthetic. J Anaesthesiol Clin Pharmacol. 28(2):205-209.
Notice of Abandonment issued Mar. 28, 2013 for U.S. Appl. No. 13/337,598, filed Dec. 27, 2011 (Inventor: Jay Richard Ray II) (2 pages).
Express Abandonment to Obtain a Refund filed Mar. 22, 2013 for U.S. Appl. No. 13/337,598, filed Dec. 27, 2011 (Inventor: Jay Richard Ray II) (1 page).
Decision on Petition issued Nov. 14, 2012 for U.S. Appl. No. 13/337,598, filed Dec. 27, 2011 (Inventor: Jay Richard Ray II) (1 page).
Petition for Express Abandonment to Obtain a Refund filed Nov. 6, 2012 for U.S. Appl. No. 13/337,598, filed Dec. 27, 2011 (Inventor: Jay Richard Ray II) (1 page).
Restriction Requirement issued Nov. 2, 2012 for U.S. Appl. No. 13/337,598, filed Dec. 27, 2011 (Inventor: Jay Richard Ray II) (9 pages).
Notice of Abandonment issued Aug. 6, 2012 for U.S. Appl. No. 13/409,738, filed Mar. 1, 2012 (Inventor: Jay Richard Ray II) (2 pages).
Decision on Petition issued Aug. 6, 2012 for U.S. Appl. No. 13/409,738, filed Mar. 1, 2012 (Inventor: Jay Richard Ray II) (1 page).
Petition for Express Abandonment to Obtain a Refund filed Aug. 1, 2012 for U.S. Appl. No. 13/409,738, filed Mar. 1, 2012 (Inventor: Jay Richard Ray II) (1 page).
Non-Final Office Action issued Mar. 4, 2016 for U.S. Appl. No. 13/564,525, filed Aug. 1, 2012 (Inventor: Jay Richard Ray II) (22 pages).
Advisory Action with AFCP 2.0 Decision issued Jul. 27, 2015 for U.S. Appl. No. 13/564,525, filed Aug. 1, 2012 (Inventor: Jay Richard Ray II) (4 pages).
Response with AFCP 2.0 Request filed Jul. 17, 2015 for U.S. Appl. No. 13/564,525, filed Aug. 1, 2012 (Inventor: Jay Richard Ray II) (11 pages).
Final Office Action issued Jun. 9, 2015 for U.S. Appl. No. 13/564,525, filed Aug. 1, 2012 (Inventor: Jay Richard Ray II) (18 pages).
Response filed May 12, 2015 for U.S. Appl. No. 13/564,525, filed Aug. 1, 2012 (Inventor: Jay Richard Ray II) (10 pages).
Non-Final Office Action issued Feb. 12, 2015 for U.S. Appl. No. 13/564,525, filed Aug. 1, 2012 (Inventor: Jay Richard Ray II) (12 pages).

(56) References Cited

OTHER PUBLICATIONS

Terminal Disclaimer filed Sep. 26, 2014 and Approval for U.S. Appl. No. 13/564,525, filed Aug. 1, 2012 (Inventor: Jay Richard Ray II) (3 pages).
Response filed Nov. 4, 2013 for U.S. Appl. No. 13/564,525, filed Aug. 1, 2012 (Inventor: Jay Richard Ray II) (10 pages).
Terminal Disclaimer filed Sep. 30, 2013 and Disapproval for U.S. Appl. No. 13/564,525, filed Aug. 1, 2012 (Inventor: Jay Richard Ray II) (3 pages).
Final Office Action issued May 23, 2013 for U.S. Appl. No. 13/564,525, filed Aug. 1, 2012 (Inventor: Jay Richard Ray II) (19 pages).
Response filed Apr. 16, 2013 for U.S. Appl. No. 13/564,525, filed Aug. 1, 2012 (Inventor: Jay Richard Ray II) (14 pages).
Non-Final Office Action issued Jan. 18, 2013 for U.S. Appl. No. 13/564,525, filed Aug. 1, 2012 (Inventor: Jay Richard Ray II) (14 pages).
Response to Restriction Requirement filed Dec. 3, 2012 for U.S. Appl. No. 13/564,525, filed Aug. 1, 2012 (Inventor: Jay Richard Ray II) (9 pages).
Restriction Requirement issued Nov. 2, 2012 for U.S. Appl. No. 13/564,525, filed Aug. 1, 2012 (Inventor: Jay Richard Ray II) (9 pages).
Response filed Nov. 24, 2015 for U.S. Appl. No. 14/609,063, filed Nov. 14, 2015 (Inventor: Jay Richard Ray II) (20 pages).
Non-Final Office Action issued Aug. 27, 2015 for U.S. Appl. No. 14/609,063, filed Nov. 14, 2015 (Inventor: Jay Richard Ray II) (15 pages).
Response to Restriction Requirement filed Jun. 4, 2015 for U.S. Appl. No. 14/609,063, filed Nov. 14, 2015 (Inventor: Jay Richard Ray II) (9 pages).
Restriction Requirement issued May 13, 2015 for U.S. Appl. No. 14/609,063, filed Nov. 14, 2015 (Inventor: Jay Richard Ray II) (5 pages).
Preliminary Amendment filed Feb. 19, 2015 for U.S. Appl. No. 14/609,063, filed Nov. 14, 2015 (Inventor: Jay Richard Ray II) (9 pages).
Non-Final Office Action issued Feb. 9, 2016 for U.S. Appl. No. 14/836,455, filed Aug. 26, 2015 (Inventor: Jay Richard Ray II) (8 pages).
Response to Restriction Requirement filed Jan. 7, 2016 for U.S. Appl. No. 14/836,455, filed Aug. 26, 2015 (Inventor: Jay Richard Ray II) (2 pages).
Restriction Requirement issued Dec. 10, 2015 for U.S. Appl. No. 14/836,455, filed Aug. 26, 2015 (Inventor: Jay Richard Ray II) (6 pages).
Restriction Requirement issued Jan. 29, 2016 for U.S. Appl. No. 14/836,491, filed Aug. 26, 2015 (Inventor: Jay Richard Ray II) (6 pages).
Response to Restriction Requirement filed Mar. 4, 2016 for U.S. Appl. No. 14/836,509, filed Aug. 26, 2015 (published as WO 2013/101949) (Inventor: Jay Richard Ray II) (8 pages).
Restriction Requirement issued Jan. 6, 2016 for U.S. Appl. No. 14/836,509, filed Aug. 26, 2015 (published as WO 2013/101949) (Inventor: Jay Richard Ray II) (7 pages).
International Search Report issued Mar. 5, 2013 for International Patent Application No. PCT/US12/71846 filed Dec. 27, 2012 (published as WO 2013/101949) (Applicant: JCDS Holdings, LLC) (4 pages).
Written Opinion issued Mar. 5, 2013 for International Patent Application No. PCT/US12/71846 filed Dec. 27, 2012 (published as WO 2013/101949) (Applicant: JCDSs Holdings, LLC) (7 pages).
International Preliminary Report on Patentability issued May 5, 2015 for International Patent Application No. PCT/US12/71846 filed Dec. 27, 2012 (published as WO 2013/101949) (Applicant: JCDS Holdings, LLC) (7 pages).
International Search Report issued Feb. 23, 2012 for International Patent Application No. PCT/US2011/054324 filed Sep. 30, 2011 (published as WO 2013/048453) (Applicant: Jay Richard Ray, II) (3 pages).
Written Opinion issued Feb. 23, 2012 for International Patent Application No. PCT/US2011/054324 filed Sep. 30, 2011 (published as WO 2013/048453) (Applicant: Jay Richard Ray, II) (6 pages).
International Preliminary Report on Patentability issued Apr. 1, 2014 for International Patent Application No. PCT/US2011/054324 filed Sep. 30, 2011 (published as WO 2013/048453) (Applicant: Jay Richard Ray, II) (7 pages).
Restriction Requirement issued Jul. 18, 2012 for U.S. Appl. No. 13/328,369, filed Dec. 16, 2011 (Inventor: Jay Richard Ray II) (6 pages).
Response to Restriction Requirement filed Aug. 2, 2012 for U.S. Appl. No. 13/328,369, filed Dec. 16, 2011 (Inventor: Jay Richard Ray II) (2 pages).
Non-Final Office Action issued Oct. 4, 2012 for U.S. Appl. No. 13/328,369, filed Dec. 16, 2011 (Inventor: Jay Richard Ray II) (7 pages).
Response filed Dec. 18, 2012 for U.S. Appl. No. 13/328,369, filed Dec. 16, 2011 (Inventor: Jay Richard Ray II) (11 pages).
Final Office Action issued Jan. 14, 2013 for U.S. Appl. No. 13/328,369, filed Dec. 16, 2011 (Inventor: Jay Richard Ray II) (10 pages).
Response filed Mar. 22, 2013 for U.S. Appl. No. 13/328,369, filed Dec. 16, 2011 (Inventor: Jay Richard Ray II) (11 pages).
Non-Final Office Action issued Feb. 5, 2014 for U.S. Appl. No. 13/328,369, filed Dec. 16, 2011 (Inventor: Jay Richard Ray II) (10 pages).
Response filed Jul. 7, 2014 for U.S. Appl. No. 13/328,369, filed Dec. 16, 2011 (Inventor: Jay Richard Ray II) (15 pages).
Final Office Action issued Oct. 6, 2014 for U.S. Appl. No. 13/328,369, filed Dec. 16, 2011 (Inventor: Jay Richard Ray II) (10 pages).
Examiner Interview Summary issued Dec. 2, 2014 for U.S. Appl. No. 13/328,369, filed Dec. 16, 2011 (Inventor: Jay Richard Ray II) (2 pages).
Notice of Appeal filed Feb. 6, 2015 for U.S. Appl. No. 13/328,369, filed Dec. 16, 2011 (Inventor: Jay Richard Ray II) (1 page).
Response filed Apr. 3, 2015 for U.S. Appl. No. 13/328,369, filed Dec. 16, 2011 (Inventor: Jay Richard Ray II) (10 pages).
Appeal Brief filed Apr. 6, 2015 for U.S. Appl. No. 13/328,369, filed Dec. 16, 2011 (Inventor: Jay Richard Ray II) (30 pages).
Advisory Action issued Apr. 17, 2015 for U.S. Appl. No. 13/328,369, filed Dec. 16, 2011 (Inventor: Jay Richard Ray II) (3 pages).
Examiner's Answer issued Sep. 16, 2015 for U.S. Appl. No. 13/328,369, filed Dec. 16, 2011 (Inventor: Jay Richard Ray II) (9 pages).
Reply Brief filed Oct. 29, 2015 for U.S. Appl. No. 13/328,369, filed Dec. 16, 2011 (Inventor: Jay Richard Ray II) (10 pages).
Docketing Notice issued Nov. 17, 2015 for U.S. Appl. No. 13/328,369, filed Dec. 16, 2011 (Inventor: Jay Richard Ray II) (2 pages).

* cited by examiner

COMPOSITION AND METHOD FOR COMPOUNDED THERAPY

CROSS-REFERENCE TO RELATED APPLICATION

This patent application is a Continuation of U.S. patent application Ser. No. 13/409,738, entitled Composition and Method for Compounded Therapy, and filed Mar. 1, 2012, which is a continuation-in-part of U.S. patent application Ser. No. 13/337,598, entitled Composition and Method for Compounded Therapy and filed Dec. 27, 2011, the entirety of which is incorporated by reference herein in its entirety.

FIELD OF THE INVENTION

The present application relates to compounded therapies. In particular, the present application relates to compositions for compounded therapy and methods of compounding medications.

BACKGROUND

Transdermal creams are employed to deliver medication to the skin of a patient. Conventional compositions intended for topical administration include EMLA cream, a eutectic mixture of lidocaine and prilocaine in an emulsified topical cream, such as disclosed by U.S. Pat. Nos. 6,299,902 and 4,562,060, which are incorporated herein by reference in their entireties. However, conventional transdermal creams may include various drawbacks, such as addressing limited medical conditions, creating adverse side effects, and/or having limited shelf lives. Additionally, conventional methods of manufacturing transdermal creams may be inefficient and/or lack precision with the amount of active ingredients, or have other drawbacks.

SUMMARY

The present embodiments may relate to topically delivered compounded medications for treatment of various ailments, such as pain, osteoarthritis, epilepsy, inflammation, muscle fatigue, spasms, and/or other ailments. In one aspect, a transdermal cream for the effective administration of multiple medications simultaneously for one or more ailments may be provided. The transdermal cream may include low concentrations of lidocaine, prilocaine, meloxicam, and lamotrigine and/or topiramate. Alternatively, the transdermal cream may include a base having lidocaine and prilocaine to which is added a fine powder of one or more medications. The medication in powder form may be generated from grinding up tablets of NSAIDs (Non-Steroidal Anti-Inflammatory Drugs), nerve depressants, anticonvulsants, antidepressants, muscle relaxants, anesthetics, and/or other active ingredients. The present embodiments also relate to methods of making the compositions discussed herein.

In one aspect, a transdermal cream that permits the simultaneous administration of multiple medications in low concentrations may be provided. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and lamotrigine in an amount between approximately 0.5% and approximately 5.0% by weight of the transdermal cream. In one embodiment, the transdermal cream may comprise approximately 2.0% by weight of both lidocaine and prilocaine, approximately 0.09% by weight meloxicam, and approximately 2.5% by weight lamotrigine. As a result, the transdermal cream may allow for the topical administration of lidocaine, prilocaine, meloxicam, and lamotrigine simultaneously during use.

In another aspect, a transdermal cream that permits the simultaneous administration of multiple medications in low concentrations may be provided. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and topiramate in an amount between approximately 0.5% and approximately 5.0% by weight of the transdermal cream. In one embodiment, the transdermal cream may comprise approximately 2.0% by weight of both lidocaine and prilocaine, approximately 0.09% by weight meloxicam, and approximately 2.5% by weight topiramate. As a result, the transdermal cream may allow for the topical administration of lidocaine, prilocaine, meloxicam, and topiramate simultaneously during use.

In another aspect, a method of compounding one or more medications with a transdermal cream for the topical administration of a compounded therapy may be provided. The method may include grinding up one or more tablets of a NSAID, an anticonvulsant, a nerve depressant, a muscle relaxant, a NMDA (N-Methyl-D-aspartate) receptor antagonist, an opiate or opioid agonist, and/or antidepressant into a fine powder of medication. The method may also include adding the fine powder of medication to a transdermal cream or base composition containing both lidocaine and prilocaine, the transdermal cream including both lidocaine and prilocaine in an amount of between approximately 0.5% and approximately 7.0% by weight of the transdermal cream, respectively. The method may include adding the fine powder of compounded medication to the starting transdermal cream or base composition in a sufficient amount such that the final transdermal cream includes the compounded medication that is ground up in a low amount of between approximately 0.01% and approximately 5.0% by weight of the transdermal cream. In one embodiment, an amount of ground up medication is added to the base composition such that the final transdermal cream contains low concentrations of several active ingredients and is approximately 2.0% by weight lidocaine, approximately 2.0% by weight prilocaine, approximately 0.09% by weight meloxicam, and approximately 2.5% by weight either lamotrigine or topiramate.

In another aspect, a method of compounding medications with a transdermal cream for the topical administration of a compounded therapy may be provided. The method may include grinding up tablets of two or more medications into a fine powder of compounded medication. The two or more compounded medications to be ground up may be selected from a NSAID, an anticonvulsant, a nerve depressant, a muscle relaxant, a NMDA receptor antagonist, a local anesthetic, an antidepressant, and an opioid or opiate agonist. The method may include adding the fine powder of compounded medication to a transdermal cream or gel such that the transdermal cream or gel allows for topical delivery of the two or more compounded medications for simultaneous treatment of two or more ailments when the transdermal cream or gel is topically applied.

In another aspect, the present embodiments may include the presence of dimethyl sulfoxide (DMSO) and/or Sterile Water for Irrigation. Alternatively, the transdermal cream of the present embodiments may be compounded to have no bulk ingredients in it. For instance, during the methods discussed herein, the DMSO may be removed and replaced with Sterile Water for Irrigation or other purified water. The transdermal cream may be essentially or entirely DMSO-free.

The above-described and other features and advantages of the present disclosure will be appreciated and understood by those skilled in the art from the following detailed description, drawings, and appended claims.

BRIEF DESCRIPTION OF THE DRAWINGS

There is shown in the drawings embodiments which are presently preferred, it being understood, however, that the invention can be embodied in other forms without departing from the spirit or essential attributes thereof.

DETAILED DESCRIPTION OF THE INVENTION

Figure 1:
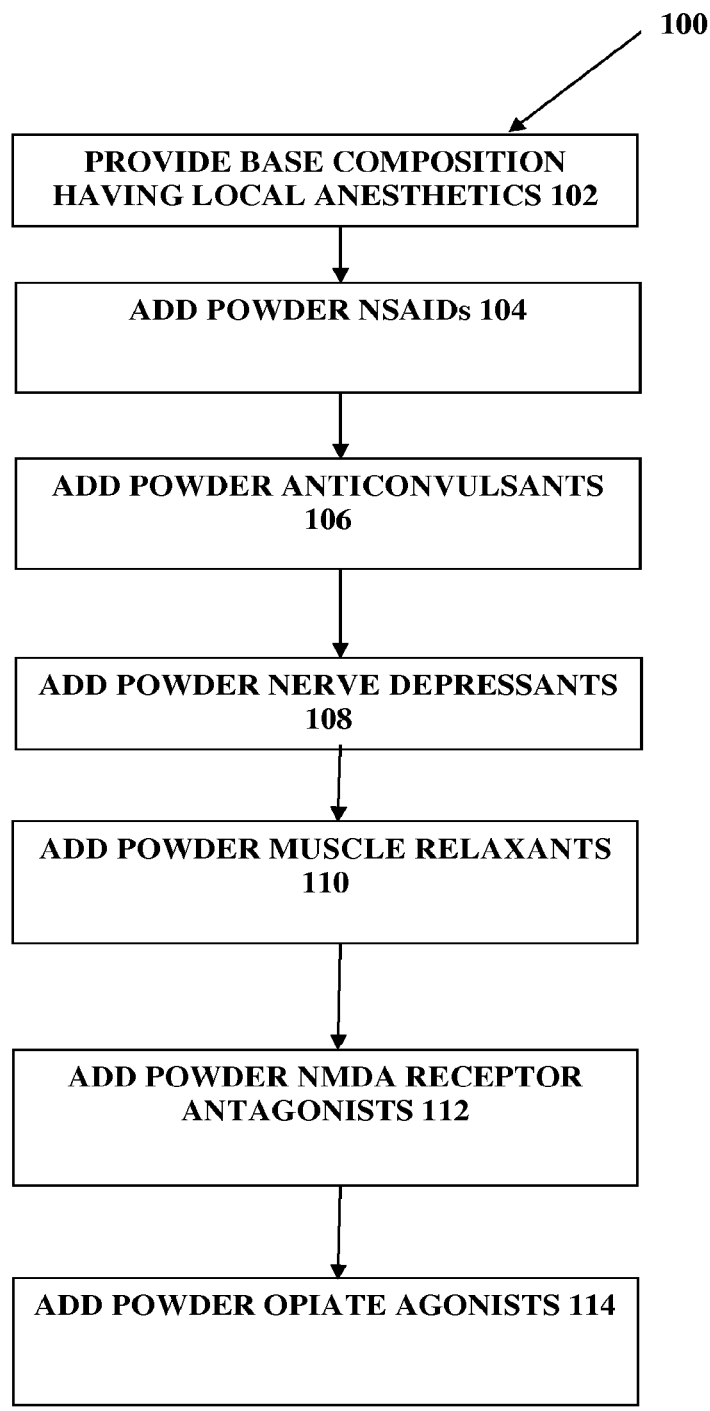
FIG. 1 depicts an exemplary method of compounding.

The present embodiments may relate to topically delivered compounded medications for treatment of various ailments, such as pain, osteoarthritis, epilepsy, inflammation, muscle fatigue, spasms, and/or other ailments. In one aspect, a transdermal cream for the effective administration of multiple medications simultaneously for one or more ailments may be provided. The transdermal cream may include low concentrations of lidocaine, prilocaine, meloxicam, lamotrigine and/or topiramate, and other active ingredients.

Alternatively, the transdermal cream may include a base having both lidocaine and prilocaine, and to which is added a fine powder of one or more medications. The medication in fine powder form may be generated from grinding up tablets of NSAIDs (Non-Steroidal Anti-Inflammatory Drugs), anticonvulsants, nerve depressants, muscle relaxants, NMDA (N-Methyl-D-aspartate) receptor antagonists, opiate or opioid agonists, antidepressants, and/or other active agents. The fine powder may allow for precise amounts of the active ingredients to be added to the base. The transdermal cream may exhibit excellent storage characteristics, and avoid separation and/or degradation of the active ingredients from the base for substantial lengths of time.

In one aspect, a transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and lamotrigine and/or topiramate in an amount between approximately 0.5% and approximately 5.0% by weight of the transdermal cream. As a result, the transdermal cream may allow for the topical administration of lidocaine, prilocaine, meloxicam, and lamotrigine and/or topiramate simultaneously during use. In one embodiment, the transdermal cream may comprise approximately 2.0% by weight lidocaine and prilocaine, respectively; approximately 0.09% by weight meloxicam; and approximately 2.5% by weight either lamotrigine or topiramate.

In another aspect, a method of compounding one or more medications with a transdermal cream for the topical administration of a compounded therapy may be provided. The method may include grinding up one or more tablets of a NSAID, an anticonvulsant, a nerve depressant, a muscle relaxant, a NMDA receptor antagonist, antidepressant, and/or an opiate or opioid agonist into a fine powder of medication. The method may also include adding the fine powder of medication to a transdermal cream containing both lidocaine and prilocaine, the transdermal cream including both lidocaine and prilocaine in an amount of between approximately 0.5% and approximately 7.0% by weight of the transdermal cream. The method may include adding the fine powder of medication to the transdermal cream in a sufficient amount such that the transdermal cream includes the medication that is ground up in an amount of between approximately 0.01% and approximately 5.0% by final weight of the transdermal cream.

The fine powder may be a fine powder of compounded medication that includes two or more active ingredients. For example, the active ingredients may comprise a NSAID, such as meloxicam, and a nerve depressant or an anticonvulsant, such as lamotrigine and/or topiramate. In one embodiment, an amount of ground up compounded medication is added to the base such that the final composition of the transdermal cream after the fine powder of compounded medication is added is approximately 2.0% by weight lidocaine, approximately 2.0% by weight prilocaine, approximately 0.09% by weight meloxicam, and approximately 2.5% by weight either lamotrigine or topiramate.

I. Compositions for Compounded Therapy

The present embodiments may relate to a compounded medication program. The compounded medication program may address several ailments simultaneously. In one aspect, the present embodiments may be intended to intended to minimize skin damage or irritation caused by the topical administration of various medications. Administering low doses or applying transdermal creams or gels with low concentrations of one or more active ingredients may minimize adverse side effects, such as side effects that develop with prolonged usage.

For instance, Stevens-Johnson Syndrome (SJS) and toxic epidermal necrolysis (TEN) are two forms of life-threatening skin conditions. SJS is a potentially deadly skin disease that usually results from a drug reaction. Drugs that have been linked to SJS include, but are not limited to: NSAIDs, allopurinol, phenytoin, carbamazepine, barbiturates, anticonvulsants, and sulfa antibiotics. However, almost any drug (prescription or over-the-counter) could potentially cause SJS if a severe enough allergy is present.

The onset of severe symptoms in drug related SJS may not appear for 1-2 weeks after first taking the drug causing the allergic reaction. Initial non-specific symptoms such as coughing, aching, headaches, fevers, vomiting, and diarrhea are commonly seen. These symptoms are usually followed by a red rash across the face and trunk of the body, later followed by blisters, and in some situations the nails and hair begin to fall out.

SJS is a very serious and potentially deadly condition and should be treated accordingly. Discontinuation of the medication and treatment of the "new infection" with a suitable antibiotic is the first step. In some situations, a patient is treated in a burn unit if necessary. However, compounded therapies may administer lower doses of active agents topically, and thus the effect of any adverse skin reaction may be lowered due to the lower doses of agent that the patient is allergic to.

In view of the foregoing, the present embodiments may include providing, within a base composition, several medications that address different ailments. The medications may be mixed in low concentrations to minimize any adverse reaction to the topical cream or gel containing the several medications.

The medications may be mixed with the base composition for topical administration to a patient. The medications may include one or more local anesthetics, such as lidocaine, prilocaine, or benzocaine; one or more NSAIDs, such as meloxicam; and one or more nerve depressants and/or anticonvulsants, such as gabapentin, topiramate, or lamotrigine. The medications may also include one or more muscle relaxants, such as baclofen or cyclobenzaprine; one or more NMDA receptor antagonists, such as ketamine; and/or one or opiate or opioid agonists, such as C2 or C3 opiate agonists, or tramadol.

II. Meloxicam/Lamotrigine/Lidocaine/Prilocaine Compounded Medication

In one aspect, a transdermal cream or gel may include lidocaine, prilocaine, meloxicam, and lamotrigine. Lidocaine and prilocaine are amide-type local anesthetic agents. They may come in commercially available creams.

The amount of lidocaine and prilocaine in the transdermal cream may be approximately the same. The amount of lidocaine and prilocaine may each be between approximately 0.5% and approximately 5.0% of the total weight of the transdermal cream. Alternatively, the amount of lidocaine and prilocaine may each be between approximately 1.0% and approximately 4.0% of the total weight of the transdermal cream, or between approximately 1.5% and approximately 3.0% of the total weight of the transdermal cream. In one preferred embodiment, the amount of lidocaine and prilocaine may each be approximately 2.0% of the total weight of the final transdermal cream or gel.

Meloxicam is a NSAID that may provide pain relief, such as pain relief for osteoarthritis or rheumatoid arthritis. In one aspect, the amount of meloxicam in the transdermal cream or gel may be less than that of the other active ingredients.

The amount of meloxicam in the transdermal cream may be between approximately 0.01% and approximately 5.0% of the total weight of the transdermal cream, or between approximately 0.03% and approximately 3.0% of the total weight of the transdermal cream. Preferably, the amount of meloxicam may be between approximately 0.05% and approximately 0.15% of the total weight of the transdermal cream. In one preferred embodiment, the amount of meloxicam may be approximately 0.09% of the total weight of the transdermal cream or gel.

Lamotrigine may be characterized as an anticonvulsant. It may be used as an antiepileptic drug to treat epilepsy or bi-polar disorders. In one aspect, the amount of lamotrigine in the transdermal cream or gel may be more than the other active ingredients, such as lidocaine, prilocaine, meloxicam, and/or other active ingredients.

The amount of lamotrigine in the transdermal cream may be between approximately 0.5% and approximately 5.0% of the total weight of the transdermal cream, or between approximately 1.5% and approximately 3.5% of the total weight of the transdermal cream. Preferably, the amount of lamotrigine may be between approximately 2.0% and approximately 3.0% of the total weight of the transdermal cream. In one preferred embodiment, the amount of lamotrigine may be approximately 2.5% of the total weight of the transdermal cream or gel.

III. Meloxicam/Topiramate/Lidocaine/Prilocaine Compounded Medication

In one aspect, a transdermal cream or gel may include lidocaine, prilocaine, meloxicam, and topiramate. The amounts of lidocaine, prilocaine, and meloxicam may be as stated above. Alternatively, other amounts of lidocaine, prilocaine, and meloxicam may be used.

Topiramate may be characterized as an antiepileptic drug used to treat epilepsy or migraines. In one aspect, the amount of topiramate in the transdermal cream or gel may be more than the other active ingredients, such as lidocaine, prilocaine, meloxicam, and/or other active ingredients.

The amount of topiramate in the transdermal cream may be between approximately 0.5% and approximately 5.0% of the total weight of the transdermal cream, or between approximately 1.5% and approximately 3.5% of the total weight of the transdermal cream. Preferably, the amount of topiramate may be between approximately 2.0% and approximately 3.0% of the total weight of the transdermal cream. In one preferred embodiment, the amount of topiramate may be approximately 2.5% of the total weight of the transdermal cream or gel.

IV. Exemplary Method of Compounding

FIG. 1 depicts an exemplary method of compounding one or more medications with a transdermal cream or gel 100. The method 100 may include providing a base composition having one or more local anesthetics 102; and adding to the base a fine powder of medication comprising: one or more NSAIDs 104; one or more anticonvulsants 106; one or more or nerve depressants 108; one or more muscle relaxants 110; one or more NMDA receptor antagonists 112; and/or one or more opiate or opioid agonists 114. The transdermal cream or gel may include additional, fewer, or alternate steps and/or ingredients.

The method 100 may comprise providing a base composition 102. The base composition may comprise one or more local anesthetics 102. Primary examples of local anesthetics that the transdermal creams and base composition disclosed herein may employ include, but are not limited to, lidocaine, prilocaine, benzocaine, and/or tetracaine. The local anesthetics may comprise between approximately 0.1% and approximately 5.0% by weight of the transdermal cream. Other amounts may be used, including those discussed elsewhere herein. The base composition may include additional, fewer, or alternate ingredients.

Preferably, the base composition may include lidocaine and/or prilocaine. In one embodiment, the base composition may comprise an equal amount of lidocaine and prilocaine, such as between approximately 2.0% and approximately 3.0% by weight of the transdermal cream. Other amounts may be used, including those discussed elsewhere herein.

The method 100 may comprise adding to the base composition a fine powder of medication that includes one or more NSAIDs 104. NSAIDs may decrease inflammation, swelling, and pain. NSAIDs that may be added to the base composition may include: (1) oxicams—meloxicam and piroxicam; (2) salicylic acid derivatives—aspirin, diflunisal, salsalate, and trilisate; (3) propionic acids—flurbiprofen, ibuprofen, ketoprofen, naproxen, and oxaprozin; (4) acetic acids—diclofenac, etodolac, indomethacin, ketorolac, nabumetone, sulindac, and tolmetin; (5) fenamates—meclofenamate; and/or (6) COX-2 inhibitors—celecoxib, rofecoxib, and valdecoxib. Preferably, the final transdermal cream may comprise a low concentration of an oxicam, such as meloxicam or piroxicam, in a low amount between approximately 0.01% and 5.0% by weight of the final transdermal cream. In one embodiment, the final transdermal cream may include approximately 0.09% meloxicam by weight. Other amounts may be used, including those discussed elsewhere herein.

The method 100 may comprise adding to the base composition a fine powder of medication that includes one or more anticonvulsants 106. Anticonvulsants that may be added to the base composition may include lamotrigine and/or topiramate. The final transdermal cream may include an anticonvulsant in a low amount between approximately 0.1% and approximately 5.0% by weight of the final transdermal cream. Preferably, the final transdermal cream may comprise approximately 2.5% of either lamotrigine or topiramate by weight. Other amounts may be used, including those discussed elsewhere herein.

The method 100 may comprise adding to the base composition a fine powder of medication that includes one or more nerve depressants 108. Nerve depressants that may be added to the base composition may include gabapentin and/or others. The low amount of nerve depressant in the transdermal cream may be between approximately 0.1% and approximately 5.0% of the total weight of the transdermal cream. Other amounts may be used.

The method 100 may comprise adding to the base composition a fine powder of medication that includes one or more muscle relaxants 110. The active ingredients that may be added to the base compositions in form of fine powder may comprise baclofen, carisoprodol, chlorzoxazone, cyclobenzaprine, dantrolene, diazepam, metaxalone, methocarbamol, orphenadrine, quinine sulfate, tizanidine, and/or other muscle relaxants. The low amount of muscle relaxant in the transdermal cream may be between approximately 0.1% and approximately 5.0% of the total weight of the transdermal cream. Other amounts may be used.

The method 100 may comprise adding to the base composition a fine powder of medication that includes one or more NMDA receptor antagonists 112, such as ketamine. Ketamine may be useful because of its NMDA receptor activity (antagonism). The low amount of NMDA receptor antagonist in the transdermal cream may be between approximately 0.1% and approximately 5.0% of the total weight of the transdermal cream. Other amounts may be used.

The method 100 may comprise adding to the base composition a fine powder of medication that includes one or more opiate or opioid agonists 114. C2 opiate agonists may include oxycodone, morphine, methadone, hydromorphone, and fentanyl. C3 opiate agonists may include hydrocodone, codeine, propoxyphene, butalbital, and pentazocine. The active ingredients that may be added to the base composition in the form of fine powder may include the C2 and C3 opiate agonists named above and/or tramadol. The low amount of opiate or opioid agonist in the transdermal cream may be between approximately 0.1% and approximately 5.0% of the total weight of the transdermal cream. Other amounts may be used.

V. Another Exemplary Method of Compounding

A method of compounding medications with a transdermal cream using a fine powder of medication is disclosed herein. In general, a base composition, such as a lidocaine/prilocaine cream, should be selected. The preparer, such as a pharmacist, should calculate the weight of powders needed. Then, the prepare should grind the medication, such as tablets containing the medication, into fine powder and weigh the ingredients. The preparer should triturate the powders together and wet with dimethyl sulfoxide (DMSO) or Sterile Water for Irrigation. The preparer should bring to total weight with the lidocaine/prilocaine cream and mix well. The mixture should be milled in an ointment mill as necessary to acquire the desired consistency. After which, the preparer should mix thoroughly and package appropriately.

Figure 2:
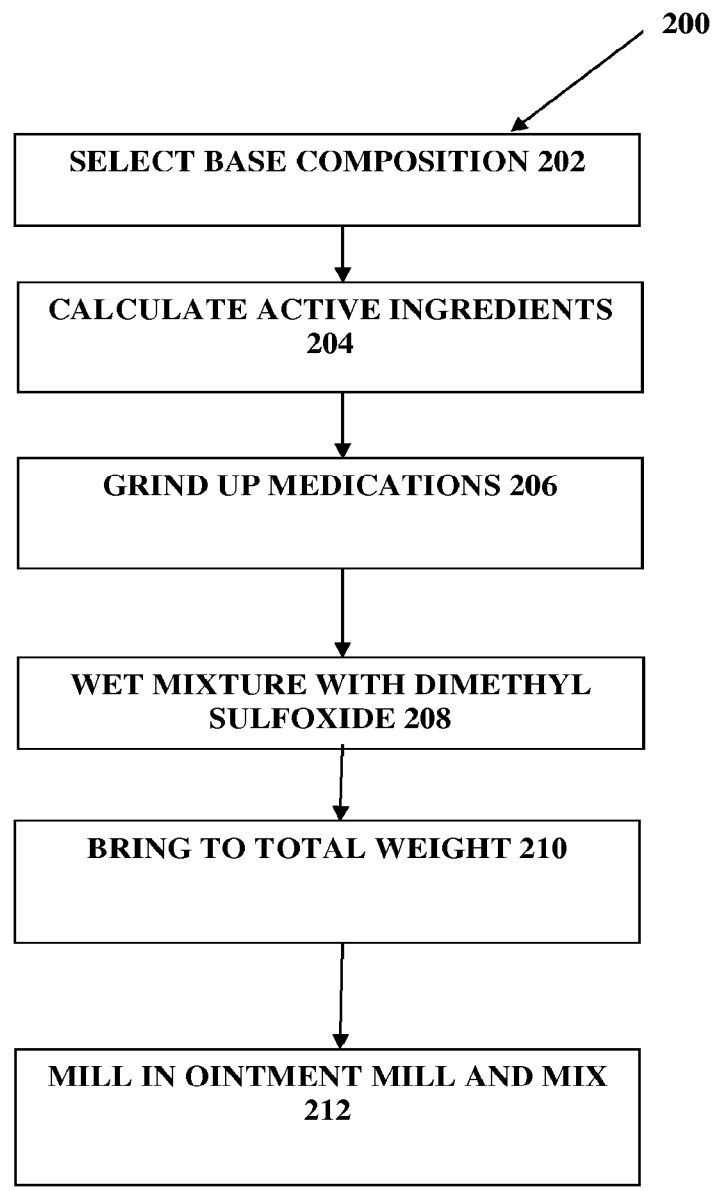
FIG. 2 depicts another exemplary method of compounding.

More specifically, FIG. 2 depicts an exemplary method of compounding medications with a transdermal cream 200. The method 200 depicted in FIG. 2 may be used to manufacture the transdermal creams discussed herein, including those discussed in relation to FIG. 1 above. The method 200 may include selecting a base composition 202; calculating an amount of active ingredients 204; grinding up the tablets containing the active ingredients 206; wetting the mixture with DMSO or Sterile Water for Irrigation 208; bringing to total weight 210; and milling in an ointment mill and mixing 212. The method 200 may include additional, fewer, or alternate actions.

The method 200 may include selecting a base composition 202 for a transdermal cream or gel. The base composition may include one or more local anesthetics, such as lidocaine and/or prilocaine. The base may include approximately equal amounts of lidocaine and prilocaine. The base composition may be a transdermal cream and may originally have approximately 2.5% lidocaine and approximately 2.5% prilocaine by weight. Other initial amounts of lidocaine and/or prilocaine may be used. In one embodiment, the base composition that includes lidocaine and/or prilocaine may be used in an amount of approximately 24,000 gm. Other amounts of base composition may be used.

The method 200 may include calculating an amount of active ingredients 204. The active ingredients may come in various size tablets. Noted herein, one of the transdermal cream embodiments, includes meloxicam and lamotrigine. For that embodiment, the ingredients may include 15 mg tablets of meloxicam, and approximately 1,500 of the 15 mg tables of meloxicam may be used. Tablets with other dosages of meloxicam may be used, and in different amounts. For instance, 7.5 mg or 30 mg tablets of meloxicam may be used.

The ingredients may also include 200 mg tablets of lamotrigine, and approximately 3,000 of the 200 mg tablets of lamotrigine may be used. Tablets with other dosages of lamotrigine may be used, and in different amounts. For instance, lamotrigine tablets ranging from 2 to 200 mg may be used.

To manufacture the transdermal cream embodiment that includes meloxicam and lamotrigine, the following formulas may be used to identify the amount of tablet powder of meloxicam and lamotrigine needed:

a. Meloxicam:

avg tab weight_____gm×tablets
   needed_____=tablet powder
   needed_____gm.

b. Lamotrigine:

avg tab weight_____gm×tablets
   needed_____=tablet powder
   needed_____gm.

The foregoing formulas may be used with the numbers stated above. For instance, the composition may require 1,500 of the 15 mg tables of meloxicam, and 3,000 of the 200 mg tablets of lamotrigine. As a result, in one embodiment, 22.5 grams of meloxicam and 600 grams of lamotrigine may be mixed with other ingredients, such as 24,000 gm of lidocaine 2.5%/prilocaine 2.5% cream, as well as 2,550 gm of dimethyl sulfoxide (DMSO). Instead of or in addition to lamotrigine, the medications added may include topiramate or other active ingredients. Instead of DMSO, Sterile Water for Irrigation may be used.

The method 200 may comprise grinding up the tablets containing the active ingredients 206. In one aspect, an automatic grinder may be used to grind up tablets containing one or more active ingredients into fine powder of medication. For instance, a Grindomix Mill may be used having a 100 volt, 60 Hz motor and five liter plastic container. The mill may have a standard lid, knife, and scraper. A five liter stainless steel container may be used that includes a knife holder. A knife of stainless steel may be used, and be autoclavable. The mill may have a plastic cover that is transparent.

The grinding up of the active ingredients into fine powder may allow for more precise amounts of each active ingredient in the final transdermal cream. This may be especially important when adding low amounts of active ingredients such that the final transdermal cream has low concentrations of various medications, which may reduce adverse allergic reactions to prolonged usage.

The method may include wetting the mixture with DMSO or Sterile Water for Irrigation 208. The DMSO and/or Sterile Water for Irrigation may facilitate the active ingredients penetrating the skin. After the ingredients in fine powder form are weighed, the preparer may triturate the powders of each ingredient together and wet with DMSO. For the 24,000 gm amount of lidocaine/prilocaine cream noted above, DMSO may be used in an amount of approximately 2,550 gm. Other amounts of DMSO may be used.

Instead of DMSO, the method may include wetting the mixture with only or primarily Sterile Water for Irrigation. Sterile Water for Irrigation USP may be a sterile, hypotonic, nonpyrogenic irrigating fluid or pharmaceutic aid (solvent), and may be composed of Sterile Water for Injection USP. It may be prepared by distillation and may contain no antimicrobial or bacteriostatic agents or added buffers. The pH may be about 5.7, or between 5.0 and 7.0. Sterile Water for Irrigation may be intended for use only as a single-dose, and may be classified as a sterile irrigant, wash, rinse, diluent and pharmaceutical vehicle. Instead of or addition to Sterile Water for Irrigation, Sterile Water for Injection or purified water may be used.

The method may include bringing to total weight with the lidocaine/prilocaine cream and mixing well 210. As noted elsewhere herein, after the fine powder of medication is mixed with the lidocaine/prilocaine base, the final transdermal cream may have approximately 2.0% by weight lidocaine, approximately 2.0% by weight prilocaine, approximately 0.09% by weight meloxicam, and approximately 2.5% by weight either lamotrigine or topiramate. The final transdermal cream may have other active ingredients as well, including those mentioned herein.

The method 200 may include milling the mixture in an ointment mill as necessary to acquire the desired consistency 212. After which, the preparer may mix the milled mixture thoroughly and package it in appropriate containers.

VI. Exemplary Storage Characteristics

The transdermal creams discussed herein that are made using fine powder of medication may exhibit excellent storage characteristics, and avoid separation and/or degradation of the active ingredients from a base composition for substantial lengths of time, such as six months or greater. For example, Table I below depicts the results of a 198 day potency test for a transdermal cream including meloxicam, lamotrigine, lidocaine, and prilocaine. As shown, there is little degradation of the active ingredients. The sample was stored in approximately 20° C. to 25° C. (68° F. to 77° F.) conditions, and contained one large white tube with cream in a clear bag.

TABLE I

198 Day Potency Test

| Analyte/Specifications | Expected Amount | Units | Results | % of EXP. | Test Method |
|---|---|---|---|---|---|
| Lamotrigine Specifications = N/A | 2.5 | % | 2.463 | 98.5% | HPLC |
| Lidocaine Specifications = N/A | 2.0 | % | 1.927 | 96.4% | HPLC |
| Meloxicam Specifications = N/A | 0.09 | % | 0.0962 | 106.9% | HPLC |
| Prilocaine Specifications = N/A | 2.0 | % | 2.118 | 105.9% | HPLC |

Table II below depicts the results of a 100 day potency test for a transdermal cream including meloxicam, topiramate, lidocaine, and prilocaine. As shown, there is little degradation of the active ingredients. The sample was stored in approximately 20° C. to 25° C. (68° F. to 77° F.) conditions, and contained one large white tube with cream in a clear bag.

TABLE II

100 Day Potency Test

| Analyte/Specifications | Expected Amount | Units | Results | % of EXP. | Test Method |
|---|---|---|---|---|---|
| Lidocaine Specifications = N/A | 2.0 | % | 1.700 | 85.0% | HPLC |
| Meloxicam Specifications = N/A | 0.09 | % | 0.0945 | 105.0% | HPLC |
| Prilocaine Specifications = N/A | 2.0 | % | 1.899 | 95.0% | HPLC |
| Topiramate Specifications = N/A | 2.5 | % | 2.368 | 94.7% | HPLC |

VII. Exemplary Methods of Compounding Using Fine Powder

An exemplary method of compounding may include grinding up tablets of one or more active ingredients into a fine powder, and then adding those ingredients in powder form to a transdermal cream or gel. The active ingredients that are ground up into a fine powder of medication may include one or more NSAIDs, anticonvulsants, nerve depressants, muscle relaxants, antidepressants, NMDA receptor antagonists, opioid or opiate agonists, local anesthetics, and/or other active agents. The transdermal cream or gel may or may not have one or more pre-existing ingredients prior to the addition of the fine powder of medication, such as one or more pre-existing local anesthetics.

The method may include grinding up tablets of one or more local anesthetics into a fine powder. The local anesthetics ground up into powder form may include lidocaine and/or prilocaine, or other agents. An amount of lidocaine and/or prilocaine powder may be added to the transdermal cream such that lidocaine comprises between approximately 0.5% and approximately 7.0% by weight of the transdermal cream, and that prilocaine comprises between approximately 0.5% and approximately 7.0% by weight of the transdermal cream. Other amounts may be used, including those discussed elsewhere herein.

The method may include grinding up tablets of one or more NSAIDs into a fine powder of medication. The NSAIDs that are ground up may include meloxicam, fluribiprofen, nabumetone, and/or other NSAIDs. The amount of NSAIDs may be between approximately 0.05% and 25.0% by weight of the transdermal cream. For instance, the transdermal cream may include meloxicam in a low amount of between approximately 0.05% and approximately 0.15% by weight of the transdermal cream, and/or flurbiprofen or nabumetone in an amount between approximately 5.0% and approximately 25.0% of the transdermal cream by weight. Other amounts may be used, including those discussed elsewhere herein.

The method may include grinding up tablets of one or more anticonvulsants into the fine powder of medication. The anticonvulsants that are ground up may include lamotrigine, topiramate, and/or other anticonvulsants. The transdermal cream may include an amount of anticonvulsant of between approximately 1.0% and approximately 5.0% by weight of the transdermal cream. Other amounts may be used, including those discussed elsewhere herein.

The method may include grinding up tablets of one or more muscle relaxants into a fine powder of medication. The muscle relaxants that are ground up may include baclofen, cyclobenzaprine, and/or other muscle relaxants. The transdermal cream may include an amount of muscle relaxant of between approximately 1.0% and approximately 5.0% by weight of the transdermal cream. Other amounts may be used, including those discussed elsewhere herein.

The method may include grinding up tablets of one or more opioid or opiate agonists into a fine powder of medication. The opioid or opiate agonists that are ground up may include C2 or C3 opiate agonists, tramadol, and/or others. The transdermal cream may include an amount of opioid or opiate agonist of between approximately 1.0% and approximately 5.0% by weight of the transdermal cream. Other amounts may be used, including those discussed elsewhere herein.

The method may include grinding up tablets of one or more NMDA receptor antagonists into a fine powder of medication. The NMDA receptor antagonists that are ground up may be ketamine and/or other antagonists. The transdermal cream may include an amount of NMDA receptor antagonist of between approximately 1.0% and approximately 40.0% by weight of the transdermal cream. Other amounts may be used, including those discussed elsewhere herein.

The method may include grinding up tablets of one or more nerve depressants into a fine powder of medication. The nerve depressants that are ground up may include gabapentin and/or other nerve depressants. The transdermal cream may include an amount of nerve depressant of between approximately 1.0% and approximately 15.0% by weight of the transdermal cream. Other amounts may be used, including those discussed elsewhere herein.

The method may include grinding up tablets of one or more tricyclic antidepressants or other antidepressants into a fine powder of medication. The tricyclic antidepressants that are ground up may include amitriptyline and/or other antidepressants. The transdermal cream may include an amount of antidepressant of between approximately 1.0% and approximately 15.0% by weight of the transdermal cream. Other amounts may be used, including those discussed elsewhere herein.

The fine powder of each active ingredient that is ground up may be added to a transdermal cream or gel separately or collectively. The medications may comprise approximately 20%, approximately 30%, or approximately 40% or more of a transdermal cream by weight. Other amounts may be used, including those discussed elsewhere herein. Alternatively, administering low doses or applying transdermal creams or gels with low concentrations of one or more active ingredients may minimize adverse side effects, such as adverse skin conditions that may develop with usage. Therefore, the method may include adding several medications in fine powder form to a transdermal cream or gel to alleviate the magnitude of any adverse skin conditions that may arise, while simultaneously providing a compounded therapy.

In specific embodiments, the two or more medications that are ground up into a fine powder may include (1) a NSAID (such as meloxicam) and an anticonvulsant (such as lamotrigine and/or topiramate); (2) a NSAID (such as fluribiprofen or nabumetone), a nerve depressant (such as gabapentin), and a muscle relaxant (such as baclofen or cyclobenzaprine); or (3) a NSAID (such as fluribiprofen or nabumetone), a nerve depressant (such as gabapentin), and an antidepressant (such as amitriptyline). Other combinations of medications may be used.

In one aspect, an amount of fine powder of several medications may be ground up and then added to a transdermal cream or gel. The several medications may include: (1) at least one local anesthetic, such as lidocaine and/or prilocaine, in an amount between approximately 1.0% and approximately 7.0% of the transdermal cream by weight; (2) at least one nerve depressant, such as gabapentin, in an amount between approximately 5.0% and approximately 15.0% of the transdermal cream by weight; (3) at least one NSAID, such as flurbiprofen or nabumetone, in an amount between approximately 5.0% and approximately 25.0% of the transdermal cream by weight; and/or (4) at least one muscle relaxant, such cyclobenzaprine, in an amount between approximately 0.5% and approximately 4.0% of the transdermal cream by weight such that multiple ailments may be addressed simultaneously. In one embodiment, the transdermal cream may comprise, by weight of the transdermal cream, approximately 2.0% lidocaine, approximately 2.0% prilocaine, approximately 6.0% gabapentin, approximately 1.0% cyclobenzaprine, and approximately 10.0% flurbiprofen or approximately 20% nabumetone. The several medications may also include an opioid or opiate agonist, a tricyclic or other antidepressant, a NMDA receptor antagonist, and/or other active ingredients.

In another aspect, an amount of fine powder of several medications may be ground up and then added to a transdermal cream or gel. The several medications may include: (1) at least one local anesthetic, such as lidocaine and/or prilocaine, in an amount between approximately 1.0% and approximately 7.0% of the transdermal cream by weight; (2) at least one nerve depressant, such as gabapentin, in an amount between approximately 5.0% and approximately 15.0% of the transdermal cream by weight; (3) at least one NSAID, such as flurbiprofen or nabumetone, in an amount between approximately 5.0% and approximately 25.0% of the transdermal cream by weight; and/or (4) at least one tricyclic antidepressant, such as amitriptyline, in an amount between approximately 0.5% and approximately 4.0% of the transdermal cream by weight. In one embodiment, the transdermal cream may comprise, by weight of the transdermal cream, approximately 2.0% lidocaine, approximately 2.0% prilocaine, approximately 6.0% gabapentin, approximately 1.0% amitriptyline, and approximately 10.0% flurbiprofen or approximately 20.0% nabumetone. The several medications may also include an opioid or opiate agonist, a muscle relaxant, a NMDA receptor antagonist, and/or other active ingredients.

In another aspect, an amount of fine powder of several medications may be ground up and then added to a transdermal cream or gel. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and lamotrigine and/or topiramate in an amount between approximately 0.5% and approximately 5.0% by weight of the transdermal cream. In one embodiment, the transdermal cream may comprise approximately 2.0% by weight of both lidocaine and prilocaine, approximately 0.09% by weight meloxicam, and approximately 2.5% by weight lamotrigine and/or topiramate. As a result, the transdermal cream or gel may allow for the topical administration of lidocaine, prilocaine, meloxicam, and lamotrigine and/or topiramate simultaneously during use. The several medications may also include an opioid or opiate agonist, a muscle relaxant, a NMDA receptor antagonist, a nerve depressant, other NSAIDs, other anticonvulsants, and/or other active agents, including those discussed elsewhere herein.

VIII. Additional Exemplary Embodiments

The present embodiments may include the presence of DMSO and/or Sterile Water for Irrigation, such as DMSO or Sterile Water for Irrigation in a sufficient quantity to allow for the topical delivery of the active ingredients mentioned herein. The transdermal cream of the present embodiments may be compounded to have no bulk ingredients in it. For instance, during the methods discussed herein, the DMSO may be removed and replaced with Sterile Water for Irrigation. The transdermal cream may be DMSO-free.

In one aspect, compounded meloxicam, topiramate (and/or lamotrigine), lidocaine, and prilocaine cream may contain strictly commercially available medications. DMSO, which may be in some cream embodiments disclosed herein, may be replaced with Sterile Water for Irrigation. Sterile Water for Irrigation may act as a primary or sole penetration enhancer in some embodiments.

Although experimentation and investigation continues, it is believed that some detriments may develop from a transition to a DMSO-free compounded transdermal cream. It is believed that the removal of DMSO from certain compounds may decrease the effectiveness of the compound given that the primary penetrant is no longer present. Also, patients that have received the previous compounded version containing DMSO may experience lower efficacy rates. It is also believed that the transition of the formula may, at best, give the same efficacy that the patients previously had experienced, and, at worst, decrease efficacy due to the absence of DMSO.

On the other hand, the use of Sterile Water for Irrigation instead of DMSO may be cheaper and involve an easier method of manufacture. Also, Sterile Water for Irrigation is an FDA-approved commercially available medication.

In one aspect, a transdermal cream that permits the simultaneous administration of multiple medications in low concentrations may be provided. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and lamotrigine in an amount between approximately 0.5% and approximately 5.0% by weight of the transdermal cream. In one embodiment, the transdermal cream may comprise approximately 2.0% by weight of both lidocaine and prilocaine, approximately 0.09% by weight meloxicam, and approximately 2.5% by weight lamotrigine. As a result, the transdermal cream may allow for the topical administration of lidocaine, prilocaine, meloxicam, and lamotrigine simultaneously during use. The transdermal cream may further include only or primarily Sterile Water for Irrigation as a penetration enhancer or other component, and be devoid of DMSO or DMSO-free.

In another aspect, a transdermal cream that permits the simultaneous administration of multiple medications in low concentrations may be provided. The transdermal cream may include lidocaine in an amount between approximately 0.5% and approximately 7.0% by weight of the transdermal cream; prilocaine in an amount between approximately 0.5% and approximately 7.0% by weight of the transdermal cream; meloxicam in an amount between approximately 0.01% and approximately 5.0% by weight of the transdermal cream; and topiramate in an amount between approximately 0.5% and approximately 5.0% by weight of the transdermal cream. In one embodiment, the transdermal cream may comprise approximately 2.0% by weight of both lidocaine and prilocaine, approximately 0.09% by weight meloxicam, and approximately 2.5% by weight topiramate. As a result, the transdermal cream may allow for the topical administration of lidocaine, prilocaine, meloxicam, and topiramate simultaneously during use. The transdermal cream may further include only or primarily Sterile Water for Irrigation for penetration enhancement or as a wetting component, and/or be devoid of DMSO or DMSO-free.

In another aspect, a method of compounding one or more medications with a transdermal cream for the topical administration of a compounded therapy may be provided. The method may include grinding up one or more tablets of a NSAID, an anticonvulsant, a nerve depressant, a muscle relaxant, a NMDA (N-Methyl-D-aspartate) receptor antagonist, an opiate or opioid agonist, and/or antidepressant into a fine powder of medication. The method may include wetting the fine powder of medication mixture with DMSO or Sterile Water for Irrigation. The method may also include adding the fine powder of medication to a transdermal cream or base composition containing both lidocaine and prilocaine, the transdermal cream including both lidocaine and prilocaine in an amount of between approximately 0.5% and approximately 7.0% by weight of the transdermal cream, respectively. The method may include adding the fine powder of compounded medication to the starting transdermal cream or base composition in a sufficient amount such that the final transdermal cream includes the compounded medication that is ground up in a low amount of between approximately 0.01% and approximately 5.0% by weight of the transdermal cream. In one embodiment, an amount of ground up medication is added to the base composition such that the final transdermal cream contains low concentrations of several active ingredients and is approximately 2.0% by weight lidocaine, approximately 2.0% by weight prilocaine, approximately 0.09% by weight meloxicam, and approximately 2.5% by weight either lamotrigine or topiramate. In one embodiment, the transdermal cream may further include only or primarily Sterile Water for Irrigation for penetration enhancement or as a wetting component, and/or be devoid of DMSO or DMSO-free.

In another aspect, a method of compounding medications with a transdermal cream for the topical administration of a compounded therapy may be provided. The method may include grinding up tablets of two or more medications into a fine powder of compounded medication. The two or more compounded medications to be ground up may be selected from a NSAID, an anticonvulsant, a nerve depressant, a muscle relaxant, a NMDA receptor antagonist, a local anesthetic, an antidepressant, and an opioid or opiate agonist. The method may include wetting the fine powder of compounded medication with DMSO or Sterile Water for Irrigation. The method may include then adding the fine powder of compounded medication to a transdermal cream or gel such that the transdermal cream or gel allows for topical delivery of the two or more compounded medications for simultaneous treatment of two or more ailments when the transdermal cream or gel is topically applied. The transdermal cream may further include only or primarily Sterile Water for Irrigation for penetration enhancement or as a wetting component, and/or be devoid of DMSO or other penetration enhancers.

The present invention may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

What is claimed is:

1. A method of making a compounded transdermal cream, the method comprising:
    grinding up one or more tablets of a Non-Steroidal Anti-Inflammatory Drug (NSAID) to produce a fine powder, wherein the NSAID comprises meloxicam;
    grinding up one or more tablets of an anticonvulsant to produce a fine powder, wherein the anticonvulsant comprises lamotrigine;
    wetting the ground fine powders with dimethyl sulfoxide (DMSO) or Sterile Water for Irrigation; and
    adding the wetted ground fine powders to a eutectic mixture of lidocaine and prilocaine in an emulsified topical cream in the form of a lidocaine 2.5%-prilocaine 2.5% cream to form a compounded transdermal cream, wherein the compounded transdermal cream comprises between 0.05% and 0.15% by weight meloxicam, between 2.0% and 3.0% by weight lamotrigine, and at least 80% by weight of the eutectic mixture comprising lidocaine and prilocaine in an emulsified topical cream in the form of a lidocaine 2.5%-prilocaine 2.5% cream, wherein the compounded transdermal cream comprises at least 2.0% by weight lidocaine and at least 2.0% by weight prilocaine.

2. The method of claim 1, wherein the compounded transdermal cream comprises approximately 0.09% by weight meloxicam.

3. The method of claim 1, wherein the compounded transdermal cream comprises approximately 2.5% by weight lamotrigine and/or topiramate.

4. The method of claim 1, wherein the compounded transdermal cream comprises 0.0 9% by weight meloxicam and 2.5% by weight lamotrigine.

5. The method of claim 1, further comprising grinding up one or more tablets of a nerve depressant, a muscle relaxant, a N-Methyl-D-aspartate (NMDA) receptor antagonist, an opiate or opioid agonist, or an antidepressant to produce a fine powder, wherein the compounded transdermal cream comprises 0.1% by weight of meloxicam and 5.0% by weight of the nerve depressant, muscle relaxant, NMDA receptor antagonist, opiate or opioid agonist, or antidepressant.

* * * * *